United States Patent [19]
Ahn et al.

[11] Patent Number: 5,856,623
[45] Date of Patent: Jan. 5, 1999

[54] PARTICLE COUNTER WITH SAMPLING PROBE HAVING ADJUSTABLE INTAKE AREA

[75] Inventors: Yo-han Ahn, Seoul; Tac-ho Kim, Pusan; Jae-jun Ryu, Seoul; Joung-sun Lee, Suwon-city, all of Rep. of Korea

[73] Assignee: Samsung Electronics Co., Ltd., Suwon, Rep. of Korea

[21] Appl. No.: 946,172

[22] Filed: Oct. 7, 1997

[30] Foreign Application Priority Data

Oct. 10, 1996 [KR] Rep. of Korea .................. 96-45095

[51] Int. Cl.$^6$ ................................................. G01N 27/00
[52] U.S. Cl. ......................................................... 73/863.03
[58] Field of Search ......................... 73/28.01, 863.02, 73/863.03, 863.51–863.61, 863.83, 864.73, 864.34, 864.81

[56] References Cited

U.S. PATENT DOCUMENTS 4,091,835   5/1978   Frampton .

*Primary Examiner*—Robert Raevis
*Attorney, Agent, or Firm*—Jones & Volentine, L.L.P.

[57] ABSTRACT

A particle counter for counting a number of particles in an air sample includes a sampling probe connected to a counter body with an intake section of the sampling probe having an adjustable area. The intake section is constructed of a plurality of telescopically interconnected shaped pieces that slide within one another to permit lengthening and shortening. The degree of lengthening or shortening determines the adjustable area of the sampling probe, which corresponds to an air speed of the air sample to provide precise particle measurements.

9 Claims, 4 Drawing Sheets

PARTICLE COUNTER WITH SAMPLING PROBE HAVING ADJUSTABLE INTAKE AREA

BACKGROUND OF THE INVENTION

1. Field of the Invention

The present invention relates to a particle counter having an adjustable probe, and more particularly, to a particle counter having an adjustable probe that is capable of reducing particle count measurement errors by varying the intake area of a sampling probe according to the speed of the air within a clean room to be measured.

2. Discussion of the Related Art

Present manufacturing processes and methods require ultra-precision, high-purity, and contamination free environments. Technology related to cleaning and reducing contaminants in the manufacturing process substantially improves the performance and the production yield of many present day products.

Clean rooms, in particular, have been used widely in many industries, including: the electronics industry for such products as semiconductors and liquid crystal displays; the precision instrument field; the chemical field, especially when manufacturing chemicals for semiconductor devices where chemical purity is important; and hospitals, medical supply factories, and the food industry where microbe pollution becomes an issue.

In particular, clean rooms in the semiconductor industry seek to control the amount of particles floating in the air so that the particles do not reach and contaminate the working object in the space. In the clean room, the temperature, humidity, interior pressure, illumination, noise and vibration, etc. are controlled and managed simultaneously. Clean room management is based on relative degrees or classes of cleanliness, as determined by the concentration and diameter of particles existing in the space.

Various measurement apparatuses have been developed to facilitate clean room management. One such measurement apparatus, a condensation particle counter, operates under the principle that the particle size increases during an alcohol evaporation process. Another measurement apparatus, an optical particle counter, measures the intensity of light scattered by the particles after projecting a laser into the sampled air containing the particles.

FIG. 1 is a perspective view showing a conventional optical particle counter. In the particle counter 10, a counter body 12 and a sampling probe 20, for sampling the air containing particles, are connected via a sampling tube 18. Formed in the counter body 12 are a display section 14, which is capable of displaying a measurement result, and an adjusting section 16, which is capable of adjusting a switch or setting a value. Also, a pump (not shown) is operated to suction the air to be measured through the sampling probe 20. A laser tube (not shown) projects the laser light into the sampling air to be measured, and a photo detector (not shown) detects the scattered laser light caused by collisions between the projected laser light and particles.

FIG. 2 is a perspective view showing the conventional sampling probe 20 of FIG. 1 in greater detail. A handle 22 is provided at the connection point between the funnel-shaped sampling probe 20 and the sampling tube 18 so that an operator can hold it while taking particle measurements. The interior wall 21 of the sampling probe 20 is flat.

In operation, a technician orients the sampling probe 20 toward a specific flow direction of the air to be measured in order to sample the air. It is preferable that the air speed as suctioned by the pump through the intake 23 of the sampling probe 20 should coincide with the air speed of the atmosphere in close proximity to the probe 20. When the air speed of the atmosphere to be measured does not coincide with the air speed at the intake 23 of the probe 20, measurement errors occur. As a result, the cleanliness management of the clean room is less than optimal.

FIGS. 3A, 3B and 3C illustrate various air flows that result according to the relationship between an interior air speed (hereinafter referred to as 'probe air speed') at the intake 23 of the probe 20 and the atmospheric air speed in close proximity to the probe 20.

FIG. 3A depicts the situation where the atmospheric air speed is greater than the probe air speed, FIG. 3B depicts the situation where the atmospheric air speed is less than the probe air speed, and FIG. 3C depicts the situation where the atmospheric air speed is equal to the probe air speed.

As shown by the arrows in FIG. 3A, when the atmospheric air speed, as generated by a clean air circulating pump (not shown) for the clean room system, is greater than the probe air speed generated by a sample suction pump within the air particle counter 10, outward eddy flows 26 are generated near the edges of the intake area 23 of the probe 20. The lower pump suction pressure causes particles that would normally have been suctioned into the probe 20 to be scattered away from the probe 20 by the outward flowing eddies 26. Accordingly, the number of particles entering the probe 20 and measured by the particle counter 10 are decreased, resulting in measurement errors and decreased reliability in the management of the clean room.

As shown by the arrows in FIG. 3B, when the atmospheric air speed, as generated by a clean air circulating pump (not shown) for the clean room system, is less than the probe air speed generated by a sample suction pump within the air particle counter 10, inward eddy flows 26 are generated near the edges of the intake area 23 of the probe 20. However, in this case, the higher pump suction pressure causes particles that would normally not have been suctioned into the probe 20 to be suctioned into the probe 20. Accordingly, the number of particles entering the probe 20 and measured by the particle counter 10 are increased, resulting in measurement errors and decreased reliability in the management of the clean room.

The preferred or optimum case would be as shown in FIG. 3C where the atmospheric air speed is equal to the probe air speed, whereby the correct amount of particles enter the probe 20, thereby minimizing measurement errors.

Present air particle counter probes have intakes that are manufactured to a general specification based on an average air speed of a typical clean room. For example, an air particle counter may be designed to sample the air at a speed of 1 cubic foot per minute according to an international standard. Accordingly, for a probe having an intake diameter of 3 cm, the probe air speed should be 0.667 m/sec for optimum results.

However, the air speeds in clean rooms for a semiconductor production are different, ranging from 0.1 m/sec to 0.7 m/sec, for example. A problem thus exists since the precise number of particles cannot be measured with the conventional fixed intake sampling probe, except for the one condition where the atmospheric air speed precisely matches the probe air speed. Since the various types of clean rooms in other industries also have different air speeds according to the type and function of the clean room, the above problem is continuously evident throughout the art.

SUMMARY OF THE INVENTION

Accordingly, the present invention is directed to a particle counter having an adjustable intake area that substantially overcomes one or more of the problems due to limitations and disadvantages of the related art.

An object of the present invention is to provide a particle counter having a single sampling probe with an adjustable intake area for measuring the number of particles within a clean room according to atmospheric air speed for the clean room.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, there is provided a particle counter for counting a number of particles in an air sample, comprising: a sampling probe connected to a particle counter body, wherein an intake section of the sampling probe has an adjustable area. The intake section is constructed of a plurality of telescopically interconnected shaped pieces that slide within one another to permit lengthening and shortening of the intake section. Telescopic or telescoping in the context of this invention refers to a sampling probe that is constructed of parts that slide within one another to permit lengthening and shortening.

Each of the shaped pieces may have a uniform thickness, or alternately, they may have a tapered thickness where the thickness of the bottom of the shaped piece is greater than a thickness of the top of the shaped piece. The shaped pieces may be substantially circular-shaped, substantially square-shaped or some other shape.

The degree of lengthening or shortening determines the adjustable area of the sampling probe, which corresponds to an air speed of the air sample to provide precise particle measurements.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which constitute a part of this specification, illustrate embodiments of the invention, in which.

DETAILED DESCRIPTION OF PREFERRED EMBODIMENT

Reference will now be made in detail to the preferred embodiments of the present invention, examples of which are illustrated in the accompanying drawings.

Figure 4:
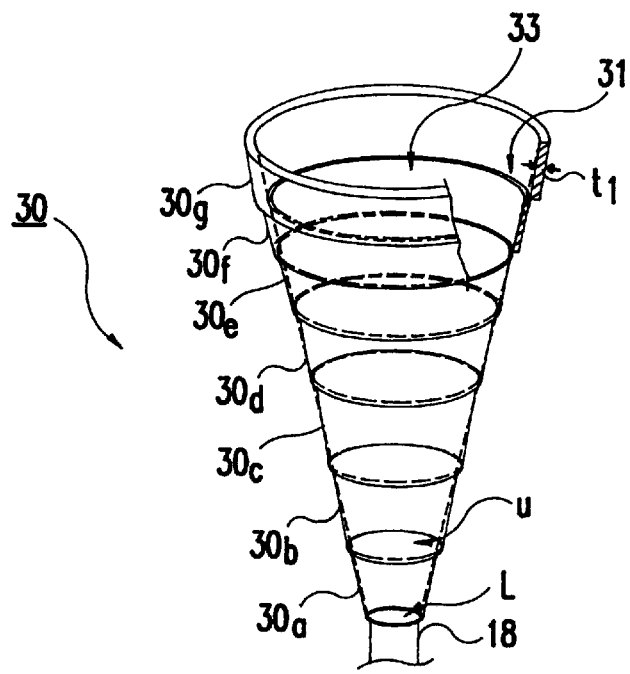
FIG. 4 is a partial cut-away perspective view of an adjustable probe in an extended state according to an embodiment of the present invention.
Figure 5:
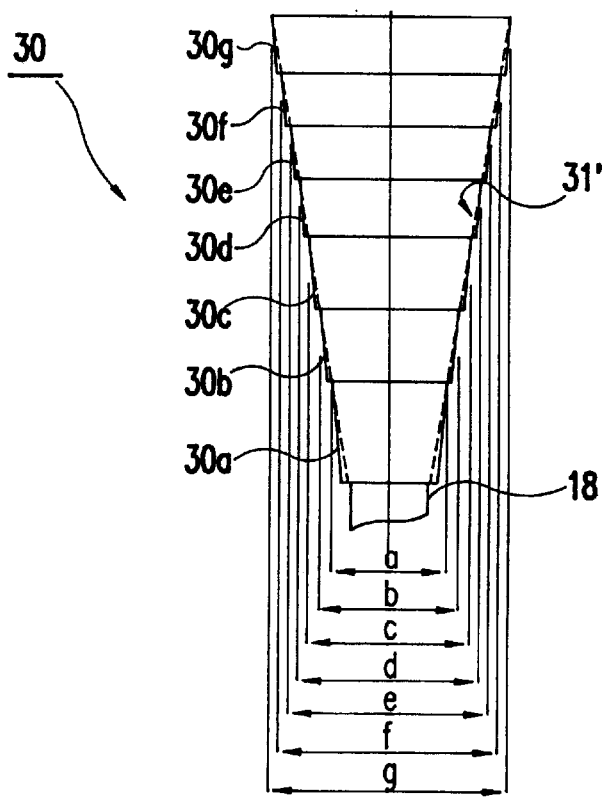
FIG. 5 is a side view showing the extended state of an adjustable probe of FIG. 4.

FIG. 4 is a partial cut-away perspective view showing an adjustable probe of the present invention in an extended state, and FIG. 5 is side view of an adjustable probe in an extended state.

Referring to FIGS. 4 and 5, a sampling tube 18 is connected at one end to an air particle counter (not shown) and to a sampling probe 30 at the other end. The probe 30 is constructed with a plurality of, for example seven, telescopically interconnected shaped pieces 30a through 30g that slide within one another to permit lengthening and shortening of an intake section 33. Telescopic or telescoping in the context of this invention refers to a sampling probe that is constructed of parts that slide within one another to permit lengthening and shortening.

Figure 7:
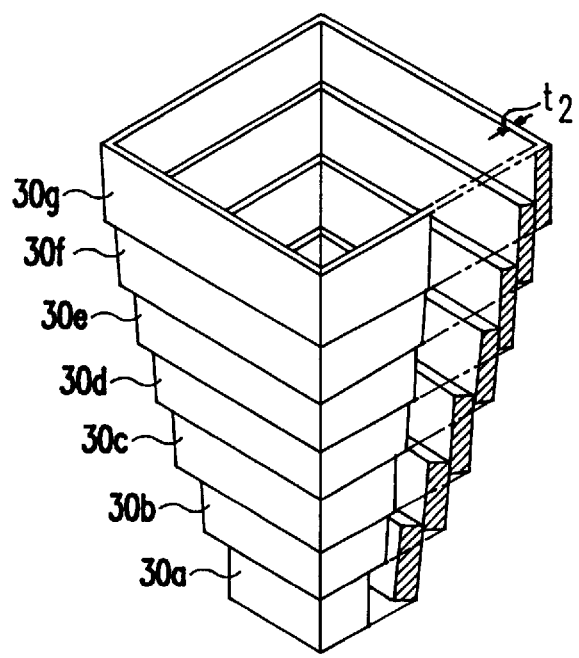
FIG. 7 is a partial cut-away perspective view of an adjustable probe in an extended state according to another embodiment of the present invention.

Of course, the present invention is not limited to seven shaped pieces, it being understood that the number of shaped pieces may be varied with the context of the present invention. Also, the shaped pieces may be circular, or square, or some other shape. The circular shape piece is shown in FIG. 4 and the square shaped piece is shown in FIG. 7. For simplicity and convenience, the invention will be described with reference to shaped pieces 30a through 30g that are substantially circular as viewed in a horizontal cross section, or in other words, substantially cylindrical as shown in the perspective view of FIG. 4.

Each of the shaped pieces 30a through 30g forms a ring with an upper area U that is greater than a lower area L, whereby each of the shaped pieces 30a through 30g are tapered from a top edge to a bottom edge. In general, the upper area U of one of the shaped pieces, for example 30e, is greater than the lower area L of an adjacent higher shaped piece, for example 30f.

More specifically, in the fully retracted sampling probe 30 position, the shaped piece 30a has a lower end, with area L, connected to the sampling tube 18 and an upper end, with a larger area U serving as the intake area 33. The intake area 33 would have a diameter "a" as shown in FIG. 5.

The next extended shaped piece 30b has a lower end connected to the upper end of shaped piece 30a, and an upper end serving as the next adjustable intake area 33 with a larger diameter "b" as shown in FIG. 5.

Extending upward, the next shaped piece 30c has a lower end connected to the upper end of shaped piece 30b, and an upper end serving as the next adjustable intake area 33 with a larger diameter "c" as shown in FIG. 5. In like fashion, shaped pieces 30d, 30e and 30f are characterized by increasing intake areas 33 corresponding to the increasing diameters "d", "e" and "f", respectively, as shown in FIG. 5.

In the fully extended position, the uppermost shaped piece 30g has a lower end connected to the upper end of shaped piece 30f, and an upper end serving as the maximum adjustable intake area 33 with the largest diameter "g" as shown in FIG. 5.

On the other hand, by successively pushing down on the sampling probe 30 as shown in FIG. 4, an operator can adjust, that is, decrease the diameter of the intake area 33.

Each of the shaped pieces 30*a* through 30*g* can have a uniform thickness "$t_1$" from top to bottom as shown in FIG. 4, which results in a step-shaped inner surface 31. On the other hand, each of the shaped pieces 30*a* through 30*g* can have a variable thickness "$t_2$", where the bottom of each shaped piece is thicker than the top of each shaped piece as best shown in FIG. 7. This results in a flat inner surface 31' as the shaped pieces are successively extended or retracted.

In all the embodiments of the present invention, since the adjacent shaped pieces have an outer diameter at the upper end that is greater than an outer diameter at the lower end of the next higher shaped piece, the shaped pieces do not fall through to the other side.

By adjusting the height of the sampling probe 30, an operator can adjust the intake area 33 accordingly. For the circular shaped sampling probe 30 as shown in FIG. 4, the probe intake area and probe diameter corresponding to atmospheric air speeds in a semiconductor clean room ranging from 0.1 m/sec to 0.7 m/sec are shown in Table 1 below.

TABLE 1

Probe Intake Area and Probe Intake Diameter as a Function of Atmospheric Air speed

| ATMOSPHERIC AIR SPEED (m/sec) | PROBE INTAKE SECTION AREA (cm$^2$) | PROBE INTAKE DIAMETER (cm) |
| --- | --- | --- |
| 0.10 | 47.19 | 7.75 |
| 0.15 | 31.46 | 6.33 |
| 0.20 | 23.60 | 5.48 |
| 0.25 | 18.88 | 4.90 |
| 0.30 | 15.73 | 4.48 |
| 0.35 | 13.48 | 4.14 |
| 0.40 | 11.80 | 3.88 |
| 0.45 | 10.49 | 3.65 |
| 0.50 | 9.44 | 3.47 |
| 0.55 | 8.58 | 3.31 |
| 0.60 | 7.87 | 3.16 |
| 0.65 | 7.26 | 3.04 |
| 0.70 | 6.74 | 2.93 |

Figure 1:
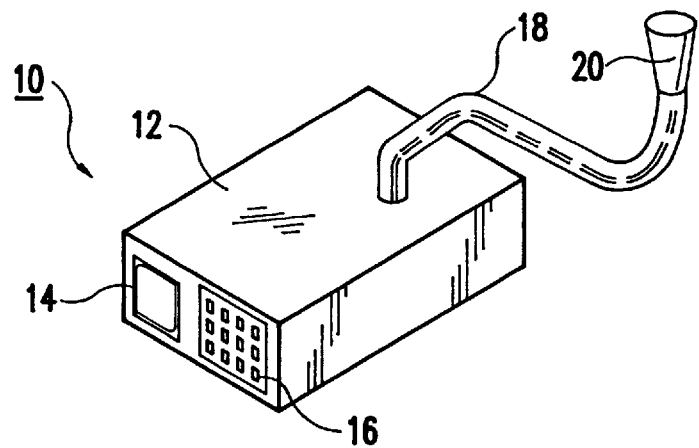
FIG. 1 is a perspective view of a conventional air particle counter.
Figure 2:
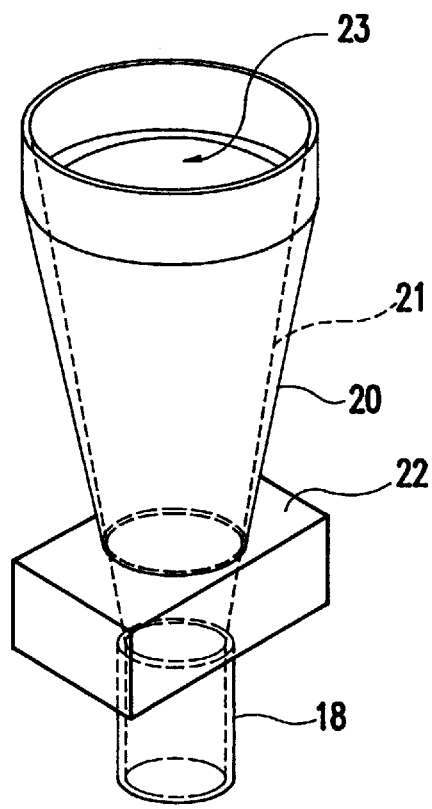
FIG. 2 is a perspective view of a sampling probe of the conventional air particle counter of FIG. 1.
Figures 3A, 3B, 3C:
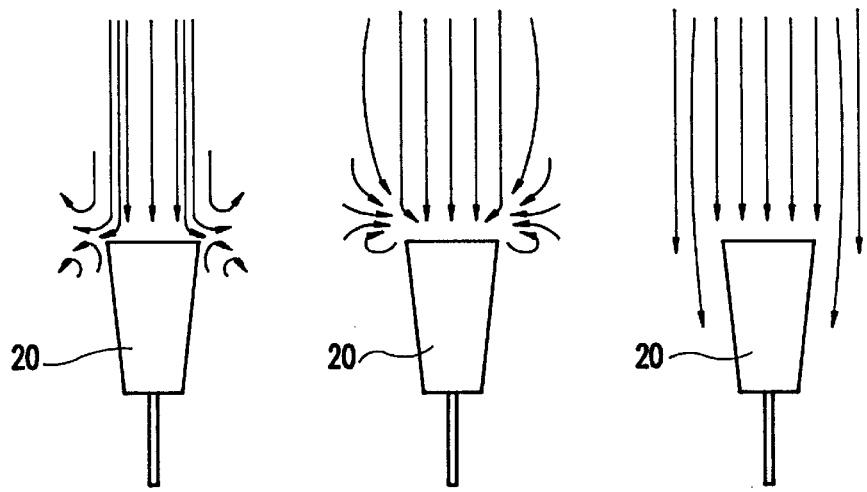
FIGS. 3A, 3B and 3C are views illustrating air flows according to a relationship between probe air speed and atmospheric air.
Figure 6:
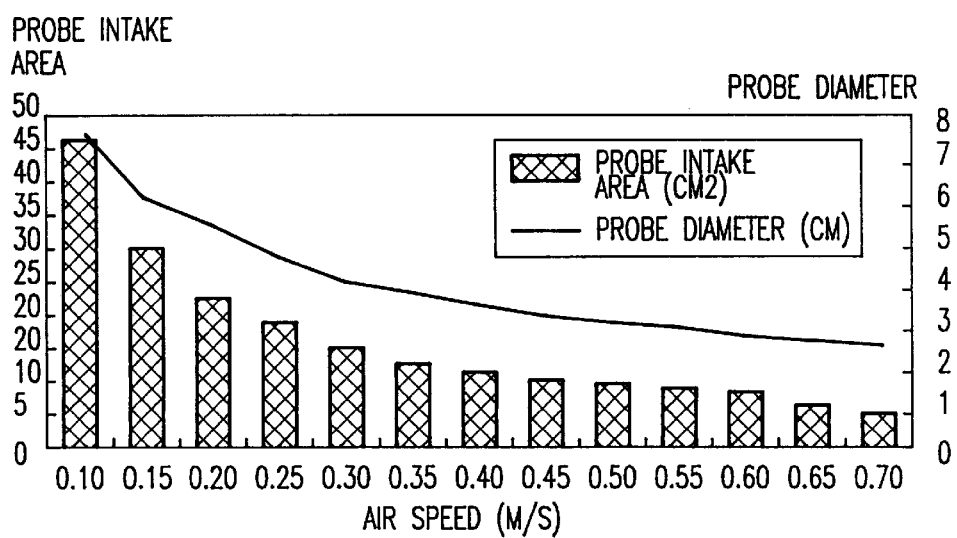
FIG. 6 is a graph showing a relationship between a probe intake area and a probe diameter according to the atmospheric air speed of a clean room.

FIG. 6 is a graph illustrating the relationship between the probe diameter and the probe intake area according to the atmospheric air speed of the clean room as provided in Table 1. As shown in Table 1 and FIG. 6, the lower the atmospheric air speed within the clean room, the larger the probe intake area should be. For example, when the atmospheric air speed is 0.1 m/sec, the preferable probe intake area is 47.19 cm$^2$ with a diameter of 7.75 cm$^2$ as shown in Table 1. In the conventional example discussed earlier in the specification, if a fixed area sampling probe having a fixed diameter of 3 cm was used at the 0.1 m/sec air speed, the particle measurement errors would be quite large.

Since the probe intake area of the sampling probe in accordance with the present invention can be easily and readily adjusted to correspond to the air speed within the clean room, particle measurement errors can be minimized. Also, the optimum probe intake area can be quickly and simply selected merely by extending or retracting the telescopically interconnected shaped pieces. Moreover, only the sampling probe itself needs to be modified to achieve the benefits of the present invention, which sampling probe can be adapted to operate with existing air particle counters.

It will be apparent to those skilled in the art that various modifications and variations can be made in the adjustable intake area sampling probe of the present invention without departing from the spirit or scope of the invention. Thus, it is intended that the present invention cover the modifications and variations of this invention that come within the scope of the appended claims and their equivalents.

What is claimed is:

1. A particle counter for counting a number of particles in an air sample, comprising:

a sampling probe connected to a particle counter body, said sampling probe having an intake section comprising a plurality of telescopically interconnected shaped pieces that slide within one another to permit lengthening and shortening of said intake section, wherein the intake section has an adjustable area.

2. The particle counter as claimed in claim 1, wherein each of said shaped pieces has an upper area that is greater than a lower area, whereby each of said shaped pieces are tapered from a top surface to a bottom surface.

3. The particle counter as claimed in claim 2, wherein the upper area of one of said shaped pieces is greater than said lower area of an adjacent higher shaped piece, measured from a bottom of said sampling probe to a top of said sampling probe.

4. The particle counter as claimed in claim 3, wherein said adjustable area of said intake section varies as said telescopically interconnected shaped pieces slide within one another to lengthen or shorten said intake section.

5. The particle counter as claimed in claim 3, wherein each of said shaped pieces has a uniform thickness, and wherein an interior wall of said sampling probe is step-shaped at connections between said upper area of said one of said shaped pieces and said lower area of said adjacent higher shaped piece.

6. The particle counter as claimed in claim 3, wherein each of said shaped pieces has a variable thickness, wherein a thickness of said bottom of said shaped piece is greater than a thickness of said top of said shaped piece, and wherein an interior wall of said sampling probe is substantially flat from said bottom of said sampling probe to said top of said sampling probe.

7. The particle counter as claimed in claim 3, wherein the adjustable area of the intake section is set to a predetermined area corresponding to an air speed of an air sample.

8. The particle counter as claimed in claim 3, wherein said shaped pieces are substantially circular-shaped.

9. The particle counter as claimed in claim 3, wherein said shaped pieces are substantially square-shaped.

* * * * *